(12) United States Patent
Sandhanasamy et al.

(10) Patent No.: US 10,111,918 B1
(45) Date of Patent: Oct. 30, 2018

(54) **METHOD OF PREPARING BIOLOGICALLY ACTIVE DERIVATIVES FROM *CALOTROPIS GIGANTEA* FLOWERS**

(71) Applicant: KING SAUD UNIVERSITY, Riyadh (SA)

(72) Inventors: Devanesan Sandhanasamy, Riyadh (SA); Mohamad Saleh Alsalhi, Riyadh (SA); Periyasami Govindasami, Riyadh (SA); Ali Kanakhir Aldalbahi, Riyadh (SA)

(73) Assignee: KING SAUD UNIVERSITY, Riyadh (SA)

( * ) Notice: Subject to any disclaimer, the term of this patent is extended or adjusted under 35 U.S.C. 154(b) by 0 days.

(21) Appl. No.: 15/911,009

(22) Filed: Mar. 2, 2018

(51) Int. Cl.
*A61K 36/24* (2006.01)
*A61K 33/24* (2006.01)
*A61K 33/34* (2006.01)
*A61K 33/26* (2006.01)
*A61K 31/695* (2006.01)
*A61K 31/22* (2006.01)
*A61K 31/216* (2006.01)
*A61K 31/5377* (2006.01)
*A61K 31/664* (2006.01)
*A61K 9/14* (2006.01)

(52) U.S. Cl.
CPC ............... *A61K 36/24* (2013.01); *A61K 9/14* (2013.01); *A61K 31/216* (2013.01); *A61K 31/22* (2013.01); *A61K 31/5377* (2013.01); *A61K 31/664* (2013.01); *A61K 31/695* (2013.01); *A61K 33/24* (2013.01); *A61K 33/26* (2013.01); *A61K 33/34* (2013.01)

(58) Field of Classification Search
CPC .................................. A61K 36/24; A61K 9/14
See application file for complete search history.

(56) References Cited

U.S. PATENT DOCUMENTS

2006/0057237 A1  3/2006  Darro et al.
2015/0366788 A1  12/2015  Mei et al.

OTHER PUBLICATIONS

Negi et al., "Ethno-Medicinal Studies at Sanchor and Mount Abu Regions Located in Sirohi District of Rajasthan," Cibtech J. of Pharma. Sci. 1(1), pp. 14-21 2012.
Patil et al., "Folk Remedies Used Against Respiratory Disorders in Jalgaon District, Maharashtra," Nat. Prod. Rad. 7(4) pp. 354-358 (2008).
Mishra, A.K., et al., P"lant Species of Delhi Flora: A Medicinal Review," Ind. J. of Plant Sci. 4(4) pp. 73-111 (2015).

*Primary Examiner* — Nicole P Babson
(74) *Attorney, Agent, or Firm* — Richard C. Litman

(57) ABSTRACT

A method of preparing biologically active derivatives from *Calotropis gigantea* flowers includes obtaining fresh *Calotropis gigantea* flowers, drying the flesh flowers, soaking the dried flowers in a natural oil, e.g., almond oil, and burning the oil-soaked flowers to provide flower ash, the flower ash including the biologically active derivatives. The flower ash can be toxin free.

14 Claims, 9 Drawing Sheets

METHOD OF PREPARING BIOLOGICALLY ACTIVE DERIVATIVES FROM *CALOTROPIS GIGANTEA* FLOWERS

BACKGROUND

1. Field

The disclosure of the present patent application relates to a method of preparing biologically active derivatives from toxic flowers, and particularly to a method of obtaining biologically active derivatives from *Calotropis gigantea* flowers.

2. Description of the Related Art

*Calotropis gigantea* is a poisonous crown flower plant, generally found in Asian countries and in some areas of the Gulf regions. Active metabolites have been extracted from different solvents including parts of the buds, flowers, and/or leaves of *Calotropis gigantea*. Some of the bioactive compounds associated with this plant include alkaloids, tannins, phenols, steroids, flavonoids, and saponins. The leaf extract of *Calotropis gigantea* has been used to treat several bacterial and viral diseases including fever, cold, indigestion, and asthma. The active metabolites have been useful as antifungal drugs.

Thus, a method of obtaining biologically active derivatives from *Calotropis gigantea* flowers solving the aforementioned problems is desired.

SUMMARY

A method of preparing biologically active derivatives from *Calotropis gigantea* flowers includes obtaining fresh *Calotropis gigantea* flowers, drying the flesh flowers, soaking the dried flowers in a natural oil, e.g., almond oil, and burning the oil-soaked flowers to provide flower ash, the flower ash including the biologically active derivatives. The flower ash can be toxin free.

These and other features of the present invention will become readily apparent upon further review of the following specification.

BRIEF DESCRIPTION OF THE DRAWINGS

Similar reference characters denote corresponding features consistently throughout the attached drawings.

DETAILED DESCRIPTION OF THE PREFERRED EMBODIMENTS

Figure 1:
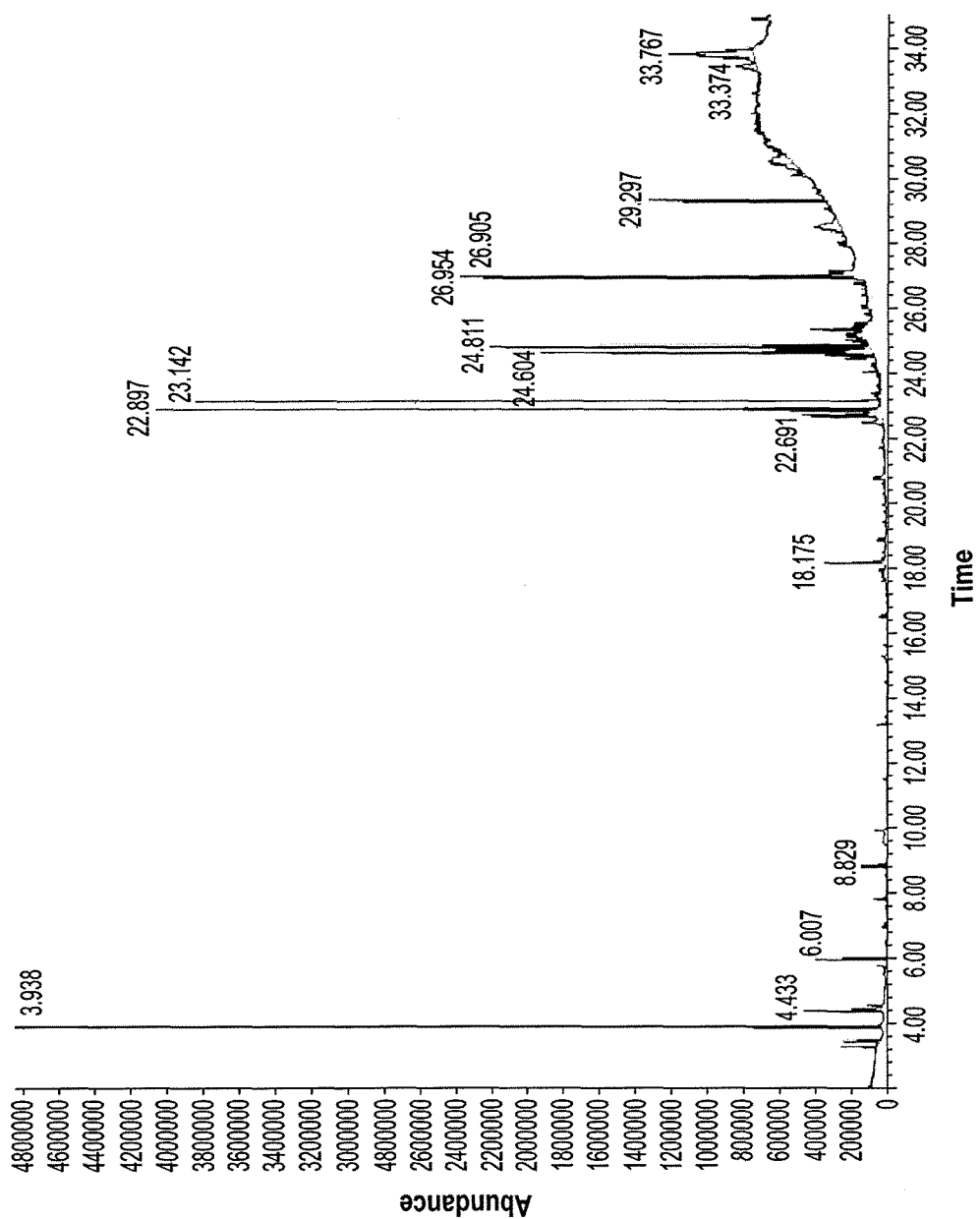
FIG. 1 shows the Gas Chromatography-Mass Spectrometry (GC-MS) spectrum of thermally treated *Calotropis gigantea* flowers.

A method of preparing biologically active derivatives from *Calotropis gigantea* flowers includes obtaining fresh *Calotropis gigantea* flowers, drying the flesh flowers, soaking the dried flowers in a natural oil, e.g., almond oil, and burning the oil-soaked flowers to provide flower ash, the flower ash including the biologically active derivatives. The fresh flowers are dried without the use of solvents. Preferably, the oil-soaked flowers are burned at a temperature of at least about 600° C., e.g., about 687° C. The flower ash can be toxin free.

The biologically active derivatives can include one or more organic compounds, such as:

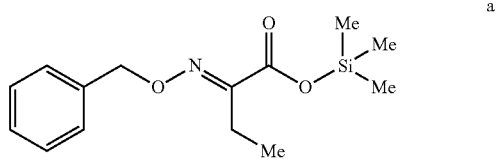 [SMILES: CC/C(=N\OCc1ccccc1)C(=O)O[Si](C)(C)C]

butanoic acid, 2-[(phenylmethoxy)imino] trimethylsilyl ester;

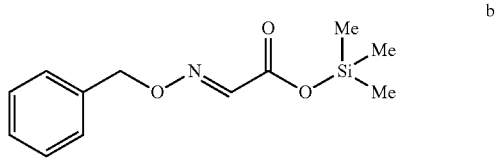 [SMILES: C[Si](C)(C)OC(=O)/C=N/OCc1ccccc1]

acetic acid 2-[(phenylmethoxy) imino] trimethylsilyl ester;

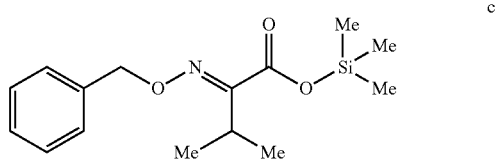 [SMILES: CC(C)/C(=N\OCc1ccccc1)C(=O)O[Si](C)(C)C]

butanoic acid, 3-[(phenylmethoxy)imino] trimethylsilyl ester;

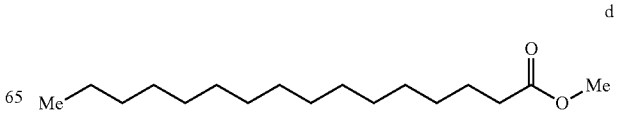

hexadecanoic acid methyl ester;

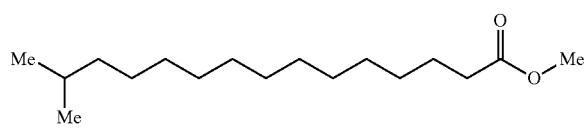

pentadecanoic acid,14-methyl-, methyl ester;

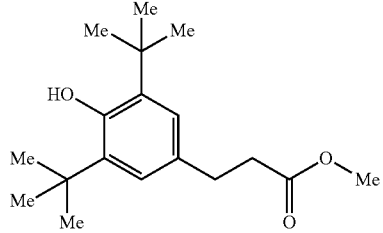

benzenepropanoic acid 3,5-bis(1,1-dimethyl)-4-hydroxyl-methyl ester;

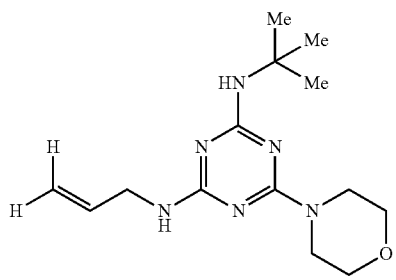

1,3,5-triazine-2-allylamino-4-tert-butylamino-6-(4-morphoyl); and

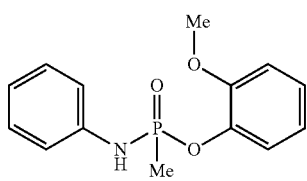

methylphosphonoamidate 1-(2-methoxyphenyl)-N-phenyl.

The biologically active derivatives can include metal nanoparticles, such as nanoparticles of Cu, $TiO_2$ and $Fe_2O_3$. The nanoparticles can have a size ranging from about 27 nm to about 32 nm.

The present method can provide biologically active compounds from toxic plant flowers, such as poisonous plant flowers of *Calotropis gigantean*, using a simple thermal method. Gas chromatography mass spectroscopy study was used for qualitative and quantitative measurements of the active compounds. Biologically active organic and inorganic compounds were found to be present in the ash materials of *Calotropis gigantea* flowers.

The biologically active compounds can be used for pharmaceuticals, preservatives in food industries to prevent the growth of unwanted microorganisms, and perfumes. For example, 2-hydroxy-4-(methylthio)butanoic acid has been effectively used in enzyme immobilization applications. The trimethylsilyl ester group in carboxylic acid has been used in many hydroboration oxidation reactions to prevent active compounds from converting to organaoborane compounds. Hexadecanoic acid methyl ester, pentadecanoic acid 14-methyl-, methyl ester, benzenepropanoic acid 3,5-bis (1,1-dimethyl)-4-hydroxyl-methyl esters have been used in many biological applications, including antimicrobial, wound healing and antiviral applications. 1,3,5-triazine 2-allylamino-4-tert-butylamnio-6-(4-morphoyl) monomers that contain chlorine atoms react with $NH_2$ or OH groups and are capable of producing double bond copolymerization. This compound was used in dental medicines as the dentin-bonding agent. The methylphosphonoamidate 1-(2-methoxyphenyl)-N-phenyl, amino compound act as a nucleic acid molecule such as RNA, DNA, oligonucleotides, mixed polymers, peptide nucleic acid and as peptides like poly-amino acid, polypeptides, proteins and nucleotides, which are used for pharmaceutical and biological compositions for the preparation of bioactive materials.

Characterization analysis for ash powder of *Calotropis gigantea* was performed using such X-ray diffraction (XRD), Fourier-transform infrared spectroscopy (FTIR), scanning electron microscopy (SEM), energy-dispersive X-ray spectroscopy (EDX) and transmission electron microscopy (SEM). Biologically active organic and inorganic compounds, as well as metallic compounds, such as Cu, $TiO_2$, and $Fe_2O_3$, were found. The metal compounds have potential biological activities, such as, antimicrobial, antiviral, antifungal, anticancer and anti-wounding properties.

The present teachings are illustrated by the following examples.

Example 1

Synthesis of Ash Powder of *Calotropis gigantea*

Ten grams of fresh flowers of *Calotropis gigantea* were collected from King Saud University campus, Riyadh, Saudi Arabia. The fresh flowers were washed five times with running tap water and washed three times with double distilled water to completely remove environmentally hazardous materials. The cleaned flowers were allowed to completely dry at room temperature under laboratory conditions. The dried flowers were soaked with almond oil (50 ml) for half an hour and then the excess oil was removed by using a shaking incubator at 45° C. for 2 hours. The flowers were then burned using a furnace at 687° C. for one hour. Finally, the burned flower ash particles were collected and stored for further analysis.

Example 2

Analysis of Ash Powder of *Calotropis gigantea*

The *Calotropis gigantea* flower ash powder was analyzed to determine the active chemical constituents by using chromatography-mass spectrometry with the methanol extract followed by WHO standard procedures. Eight major abundant active phytochemical organic compounds were identified with different retention times, which have been used for biological activities in many pharmaceutical industries.

The GCMS method was used for the analysis of the ash obtained by thermally burned *Calotropis gigantea* flowers at 687° C. FIG. 1 shows the GCMS spectrum of the thermally treated flowers in methanol having abundant peaks at various retention times (RT). Among the various components present in the chromatogram, RT=3.933, 22.894, and 23.142 are the most abundant components. Also, the corresponding RT peaks were analyzed and identified with NIST08.L and W8N08.L libraries. RT=3.933 shows three components and all three components show m/z=91, which is the molecular ion peak of the highly stable tropylium ion form of the benzyl group. Also, m/z=73 is one of the major fragments in all components of the trimethylsilyl group. All the analogues compared with NIST08.L and W8N08.L libraries are based on the RT.

Figure 2A:
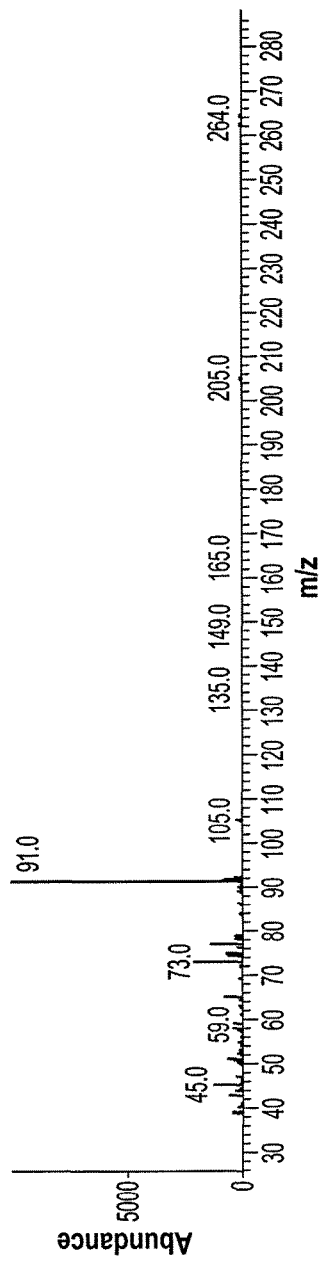
FIG. 2A shows the molecular mass spectrum fragmentations of Compound (a) present at RT=3.933.
Figure 2B:
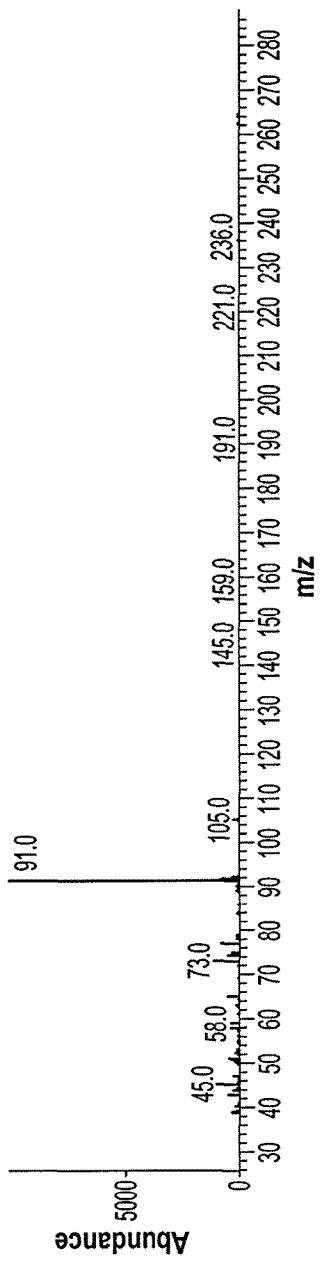
FIG. 2B shows the molecular mass spectrum fragmentations of Compound (b) present at RT=3.933.
Figure 2C:
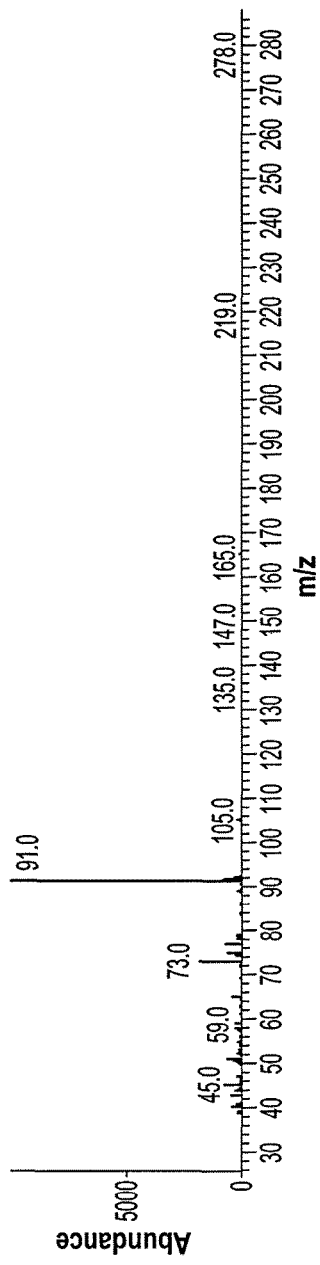
FIG. 2C shows the molecular mass spectrum fragmentations of Compound (c) present at RT=3.933.

FIG. 2A shows the molecular mass spectrum fragmentations of Compound (a) present at RT=3.933. FIG. 2B shows the molecular mass spectrum fragmentations of Compound (b) present at RT=3.933. FIG. 2C shows the molecular mass spectrum fragmentations of Compound (c) present at RT=3.933.

Figures 3A, 3B:
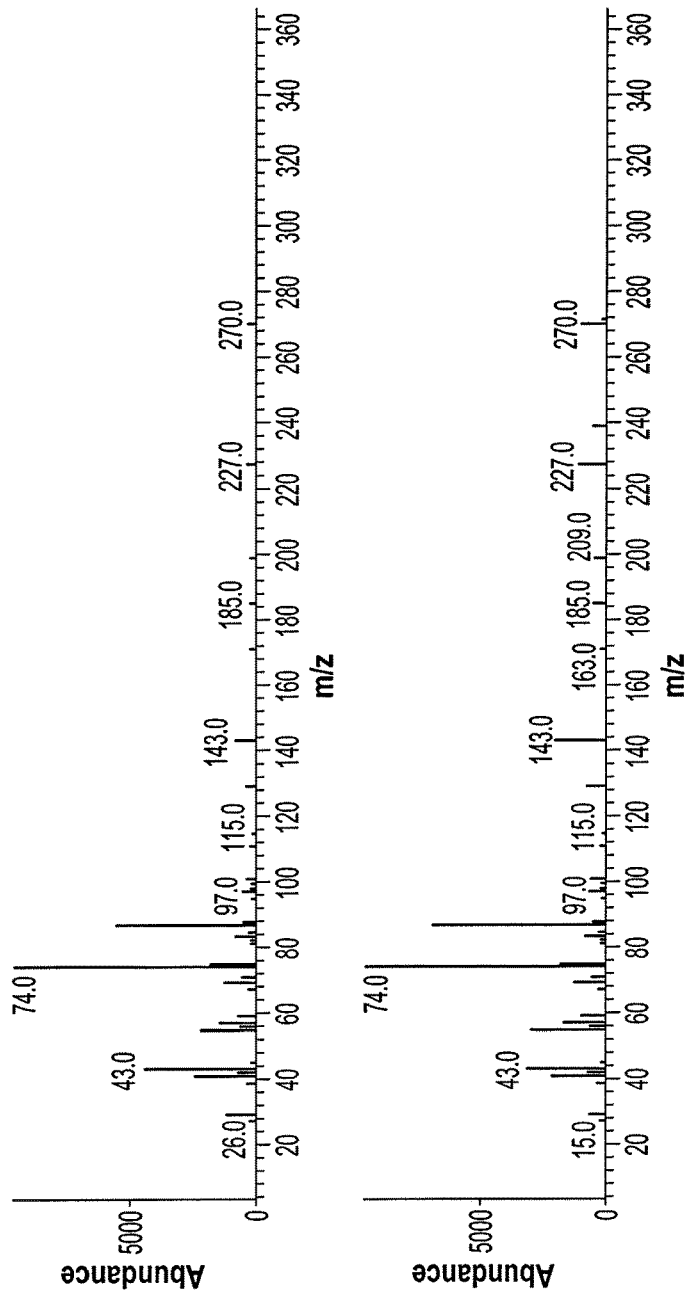
FIG. 3A shows the molecular mass spectrum fragmentations of Compound (d).
FIG. 3B shows the molecular mass spectrum fragmentations of Compound (e).

The other most abundant peak, at RT=22.894, shows two aliphatic long chain methyl esters and their molecular ion peak at m/z=74 and another major peak at m/z=43 represents methyl acetate and carbon dioxide, respectively. Mass spectrum for compound (d) present at RT=22.894 is shown in FIG. 3A. Mass spectrum for compound (e) present at RT=22.894 is shown in FIG. 3B.

Figure 4A:
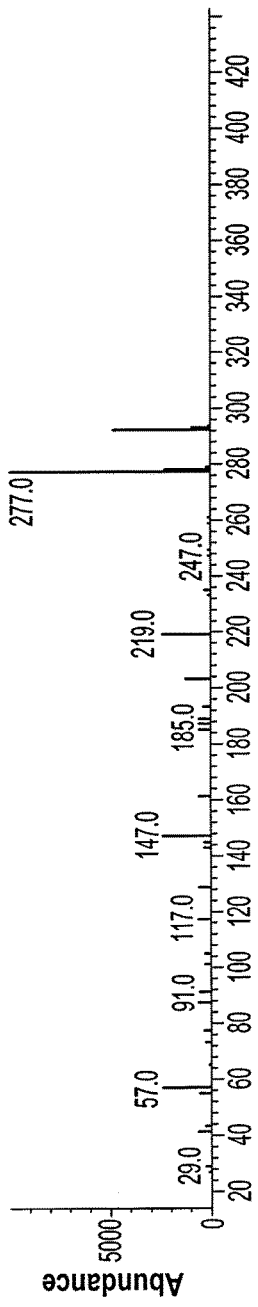
FIG. 4A shows molecular mass spectrum fragmentations of Compound (f).
Figure 4B:
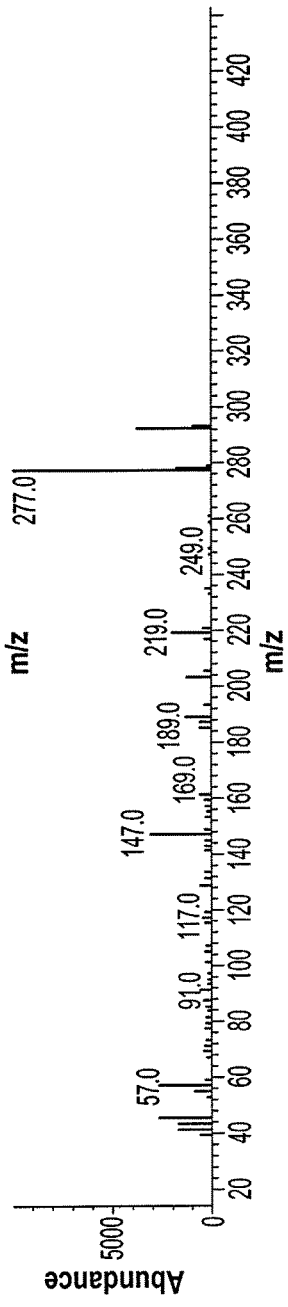
FIG. 4B shows molecular mass spectrum fragmentations of Compound (g).
Figure 4C:
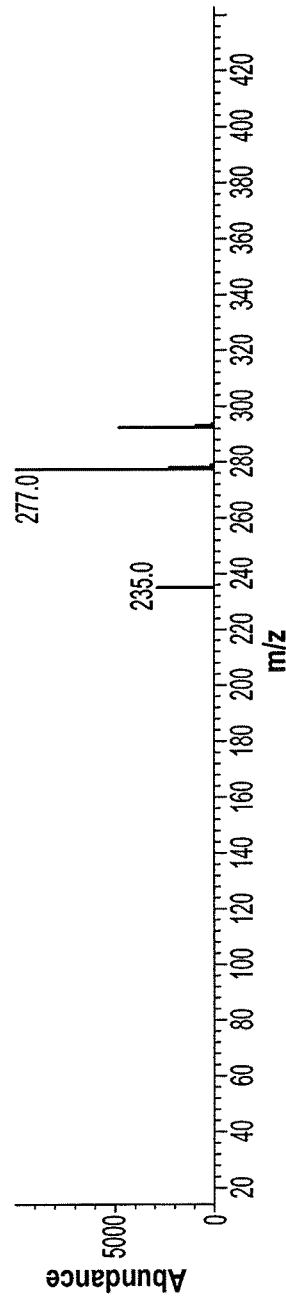
FIG. 4C shows molecular mass spectrum fragmentations of Compound (h).

The next most abundant component at RT=23.142 shows that there are three aromatic compounds present and they show m/z=277 as the molecular ion peak which is due to the loss of methyl ion during ionization. The formation of the remaining major fragments is due to the loss of the methyl group and tert-butyl groups present in the molecules. FIGS. 4A-4C show molecular mass spectrum fragmentations of components present at RT=23.142. FIG. 4A shows molecular mass spectrum fragmentations of Compound (f). FIG. 4B shows molecular mass spectrum fragmentations of Compound (g). FIG. 4C shows molecular mass spectrum fragmentations of Compound (h).

Figure 5:
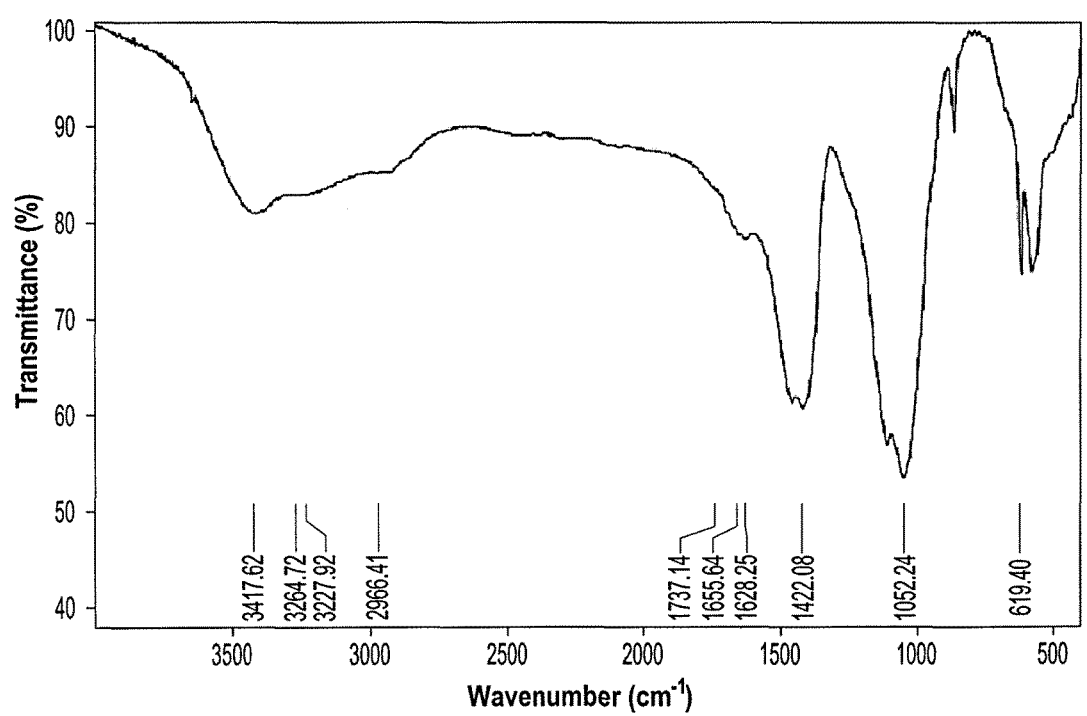
FIG. 5 shows the FTIR spectrum of thermally prepared *Calotropis gigantea* flower ash powder.

The Fourier-transform infrared (FTIR) spectrum of well dried thermally burned *Calotropis gigantea* flower ash powder is shown in FIG. 5. The absorption bands at 3427 cm$^{-1}$, 3090 cm$^{-1}$ and 2928 cm$^{-1}$ correspond to the stretching frequencies of O—H and =C—H, which shows the presence of aromatic and alcoholic functional groups in the molecules. Also the variations of two intense bands that correspond to the standard 1,3,5-triazine at 1422 cm$^{-1}$ and 1052 cm$^{-1}$ is evident for the presence of 1,3,5-substitutions in the triazine ring. A weak absorption at 874 cm$^{-1}$ corresponds to the O—Si stretching frequency. The absorption band at range of 500 cm$^{-1}$ to 550 cm$^{-1}$ is evident for bending vibrational absorption of alkyl halide groups.

Figure 6:
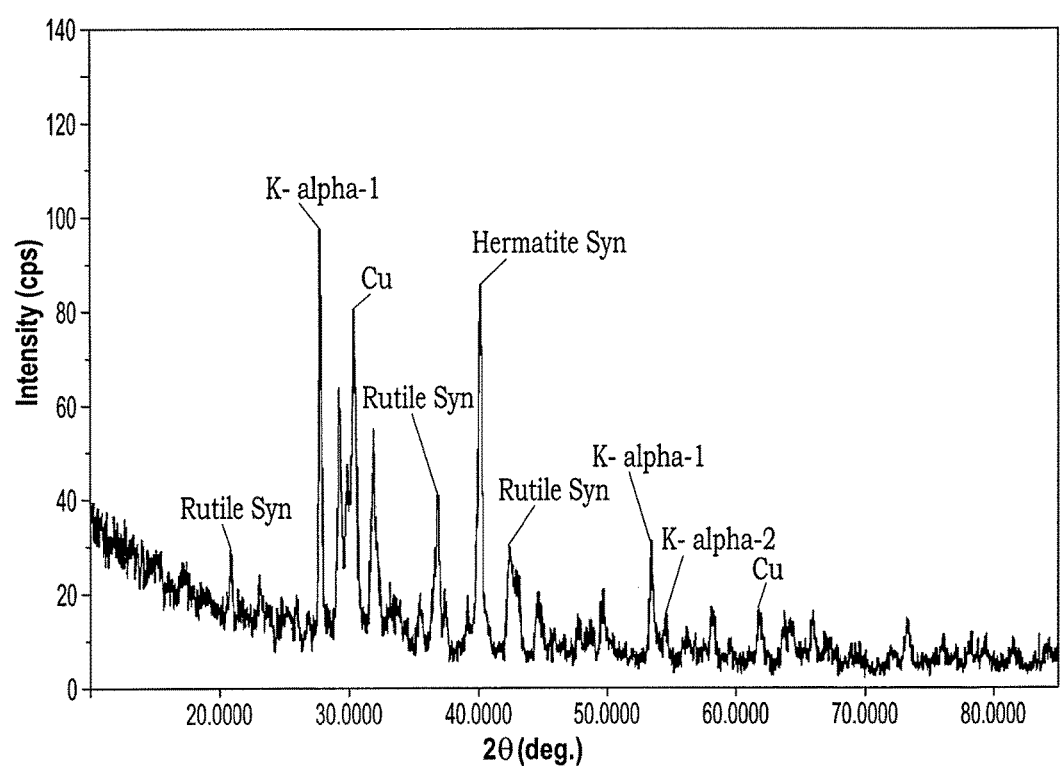
FIG. 6 shows the XRD pattern of thermally prepared *Calotropis gigantea* flower ash powder.

The X-ray Diffraction (XRD) pattern was obtained using a PANalytical X-ray diffractometer with a scan speed of 20-80 with 2θ. The XRD image is shown in FIG. 6. From the XRD pattern, it was found that the inorganic metal compounds rutile Syn(TiO$_2$), K-alpha 1 and 2 (Cu) and hematite Syn (Fe$_2$O$_3$) are in thermally synthesized ash flower powder of *Calotropis gigantea*.

Figure 7:
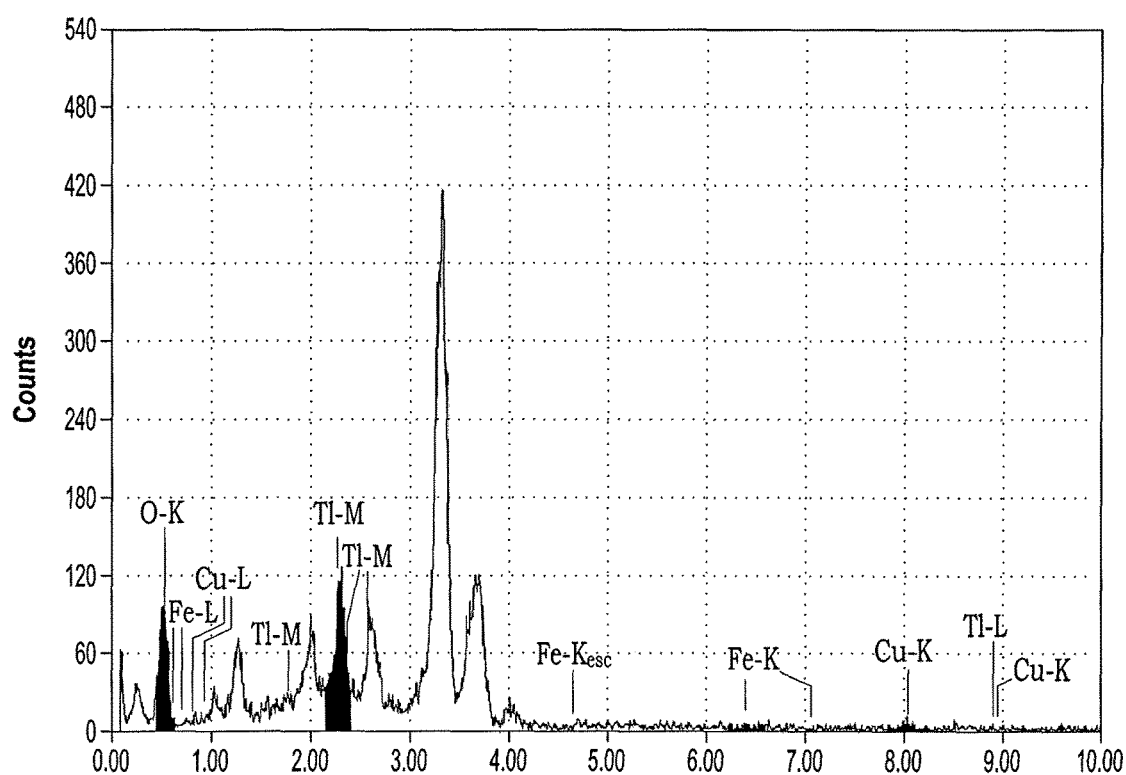
FIG. 7 shows the EDX spectrum of thermally prepared *Calotropis gigantea* flower ash powder.

Energy dispersive spectroscopy (EDX) was used for quantitative and qualitative analyses of active components from mixture of samples. FIG. 7 shows the EDX spectrum of *Calotropis gigantea* ash flower powder. The EDX report confirmed the percentage of inorganic compounds. The report proved the presence of Cu, TiO$_2$ and Fe$_2$O$_3$ in ash powder of *Calotropis gigantea*. The EDX report and the XRD results both proved the presence of metal ions from thermally synthesized samples.

Figure 8:
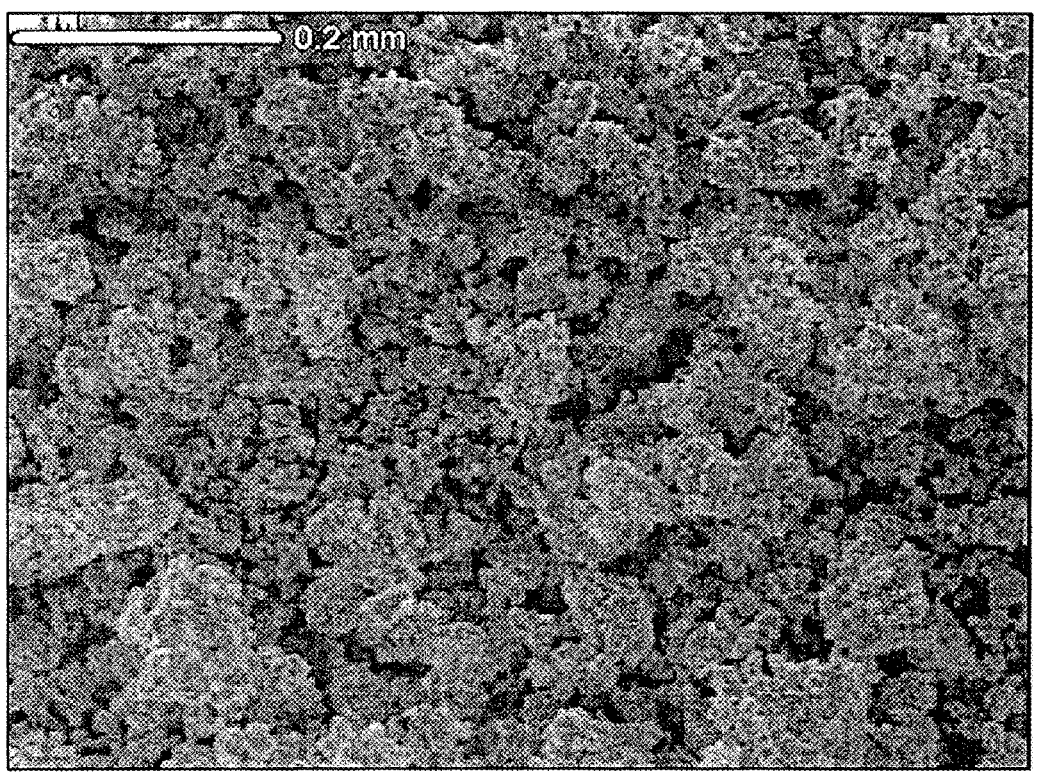
FIG. 8 shows the SEM image of *Calotropis gigantea* flower ash powder.

SEM was used to determine the active compounds and the size of the mixture complex of samples. FIG. 8 shows the SEM image, which shows the size of particles is less than 100 nm and also showed crystalline structure of Cu, TiO$_2$ and Fe$_2$O$_3$ of thermally prepared samples of *Calotropis gigantea* flower ash powder. Accordingly, in addition to organic compound groups, inorganic metal compounds were isolated in the toxic plant flower of *Calotropis gigantean*.

Figure 9:
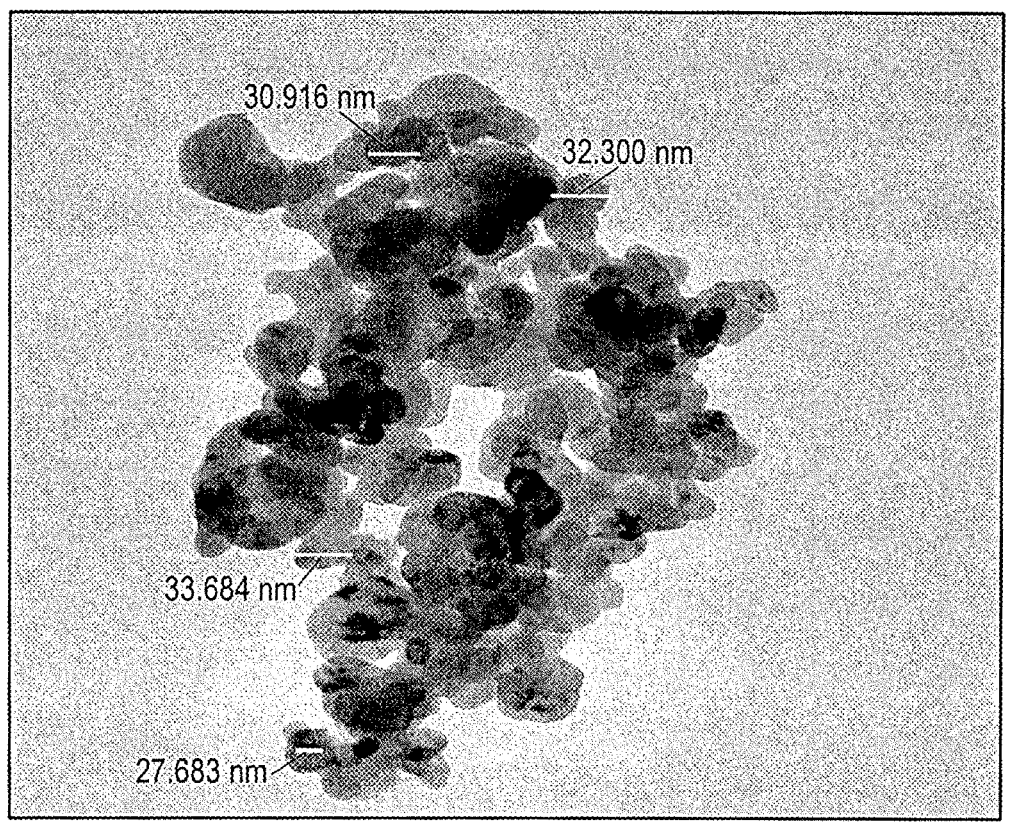
FIG. 9 shows the TEM image of *Calotropis gigantea* flower ash powder.

FIG. 9 shows the TEM image of *Calotropis gigantea* flower ash powder. The image revealed that particle sizes ranged from a minimum size of 27 nm to a maximum size of 32 nm. The TEM image provides additional supportive evidence for the presence of inorganic metal compounds that are nano sized.

It is to be understood that the method of preparing biologically active derivatives from *Calotropis gigantea* flowers is not limited to the specific embodiments described above, but encompasses any and all embodiments within the scope of the generic language of the following claims enabled by the embodiments described herein, or otherwise shown in the drawings or described above in terms sufficient to enable one of ordinary skill in the art to make and use the claimed subject matter.

We claim:

1. A method of preparing biologically active derivatives from *Calotropis gigantea* flowers, comprising:
    obtaining *Calotropis gigantea* flowers;
    drying the *Calotropis gigantea* flowers to provide dried flowers;
    soaking the dried flowers in an oil to provide oil-soaked flowers; and
    burning the oil-soaked flowers at a temperature of at least about 600° C., to provide flower ash, the flower ash including biologically active derivatives.

2. The method of preparing biologically active derivatives from *Calotropis gigantea* flowers according to claim 1, wherein the oil is almond oil.

3. The method of preparing biologically active derivatives from *Calotropis gigantea* flowers according to claim 1, wherein the biologically active derivatives comprise one or more organic compounds selected from the group consisting of:

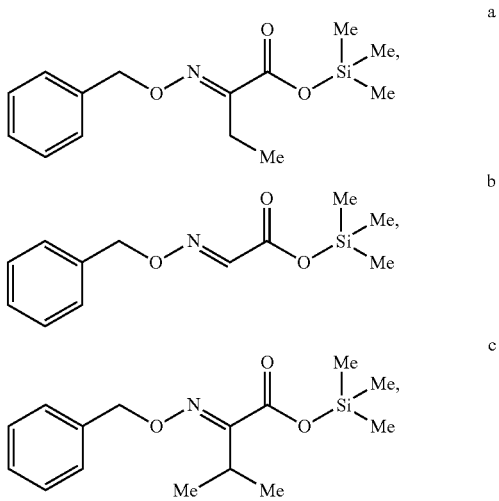

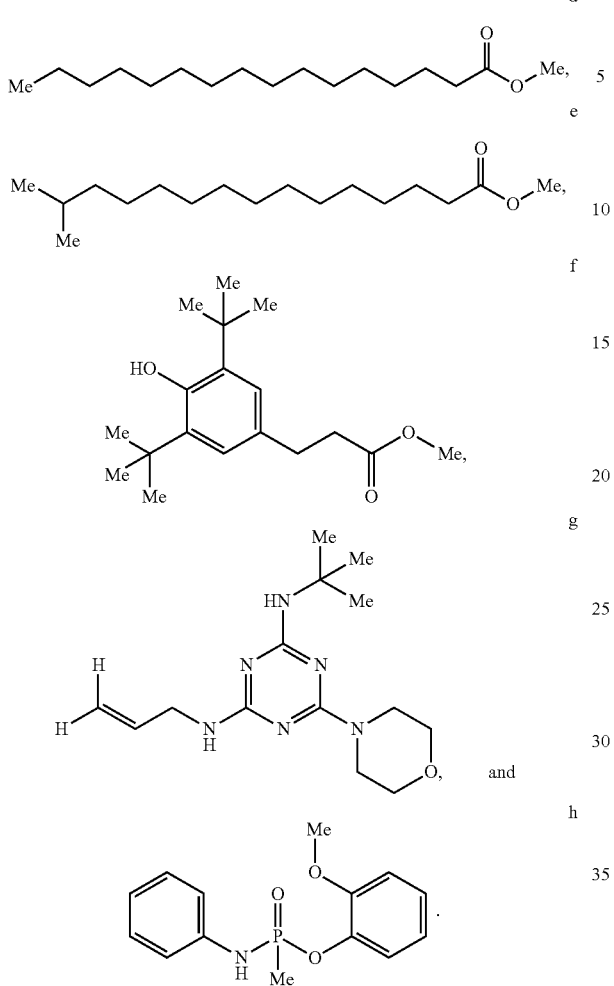

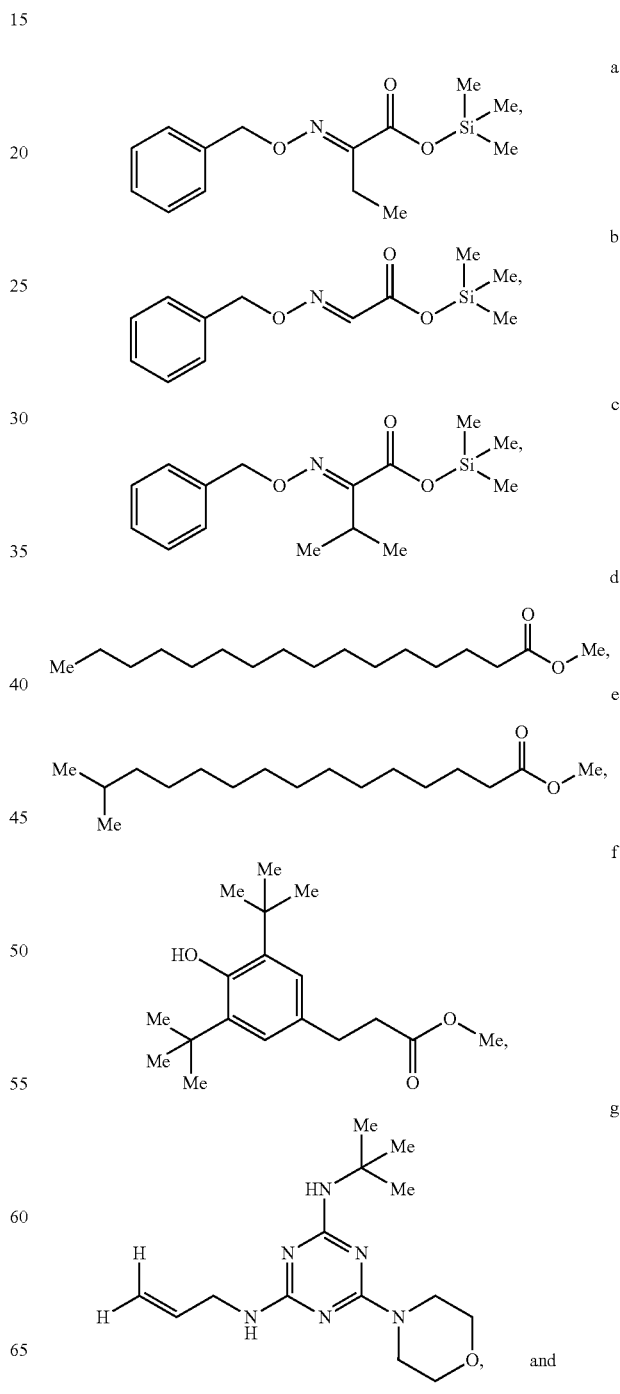

4. The method of preparing biologically active derivatives from *Calotropis gigantea* flowers according to claim 1, wherein the biologically active derivatives comprise one or more metal nanoparticles selected from the group consisting of Cu, $TiO_2$ and $Fe_2O_3$.

5. The method of preparing biologically active derivatives from *Calotropis gigantea* flowers according to claim 4, wherein the nanoparticles have a size ranging from about 27 nm to about 32 nm.

6. The method of preparing biologically active derivatives from *Calotropis gigantea* flowers according to claim 1, wherein the dried flowers are soaked in the oil for about thirty minutes.

7. The method of preparing biologically active derivatives from *Calotropis gigantea* flowers according to claim 6, further comprising removing excess oil from the oil-soaked flowers using a shaking incubator at a temperature of about 45° C. for about 2 hours.

8. The method of preparing biologically active derivatives from *Calotropis gigantea* flowers according to claim 1, wherein the flowers are burned at a temperature of about 687° C.

9. The method of preparing biologically active derivatives from *Calotropis gigantea* flowers according to claim 8, wherein the flowers are burned for about one hour.

10. A method of preparing biologically active derivatives from *Calotropis gigantea* flowers, comprising:

obtaining *Calotropis gigantea* flowers;

drying the *Calotropis gigantea* flowers to provide dried flowers;

soaking the dried flowers in almond oil to provide oil-soaked flowers; and burning the oil-soaked flowers to provide flower ash, the flower ash including biologically active derivatives.

11. The method of preparing biologically active derivatives from *Calotropis gigantea* flowers according to claim 10, wherein the biologically active derivatives comprise one or more organic compounds selected from the group consisting of:

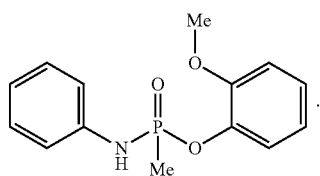
h

12. The method of preparing biologically active derivatives from *Calotropis gigantea* flowers according to claim 10, wherein the biologically active derivatives comprise one or more metal nanoparticles selected from the group consisting of Cu, $TiO_2$ and $Fe_2O_3$.

13. The method of preparing biologically active derivatives from *Calotropis gigantea* flowers according to claim 12, wherein the nanoparticles have a size ranging from about 27 nm to about 32 nm.

14. The method of preparing biologically active derivatives from *Calotropis gigantea* flowers according to claim 10, further comprising removing excess oil from the oil-soaked flowers using a shaking incubator at a temperature of about 45° C. for about 2 hours.

* * * * *